United States Patent [19]

Miller et al.

[11] Patent Number: 5,216,007
[45] Date of Patent: Jun. 1, 1993

[54] SUBSTITUTED ETHYLENE IMIDAZOLE AND TRIAZOLES

[75] Inventors: George A. Miller, Maple Glen, Pa.; Hak-Foon Chan, Walnut Creek, Calif.

[73] Assignee: Rohm and Haas Company, Philadelphia, Pa.

[21] Appl. No.: 823,041

[22] Filed: Jan. 15, 1992

Related U.S. Application Data

[63] Continuation of Ser. No. 307,414, Oct. 1, 1980, abandoned.

[51] Int. Cl.$^5$ .................. A01N 43/50; A01N 43/653; C07D 249/08; C07D 233/60
[52] U.S. Cl. .................... 514/383; 514/184; 514/396; 514/399; 548/101; 548/262.2; 548/267.2; 548/267.4; 548/267.8; 548/268.4; 548/335; 548/341
[58] Field of Search .................. 548/101, 262.2, 267.2, 548/267.4, 267.8, 268.4, 335, 341; 514/184, 383, 396, 399

[56] References Cited

U.S. PATENT DOCUMENTS

| | | | |
|---|---|---|---|
| 3,870,726 | 3/1975 | Jager et al. | 548/262 |
| 4,085,209 | 4/1978 | Miller et al. | 548/335 |
| 4,104,399 | 8/1978 | Pommer et al. | 424/269 |
| 4,213,990 | 7/1980 | Frick et al. | 424/269 |
| 4,328,348 | 5/1982 | Ogata et al. | 542/468 |

FOREIGN PATENT DOCUMENTS 2833194 2/1980 Fed. Rep. of Germany ...... 424/269

OTHER PUBLICATIONS

Worthington et al, Chem. Abstracts, vol. 97, Abstract No. 92289e (1982).
Gist-Brocades N.V., Chem. Abstracts, vol. 97, Abstract No. 92276y (1982).
Burger, Medicinal Chemistry (Second Edition, New York, 1960).
Cooper et al, J. Chem. Soc., Perkin I, (1976), pp. 545-549.
Horsfall, Fungicides and Their Action, (Waltham, Mass., 1945), p. 151.

Primary Examiner—Patricia L. Morris
Attorney, Agent, or Firm—Terry B. Morris

[57] ABSTRACT

This invention relates to substituted ethylenic imidazoles and triazoles, their enantiomorphs, acid addition salts and metal complexes as well as their methods of preparation and use as broad spectrum systemic fungicides useful in controlling phytopathogenic fungi such as barley net blotch (*Helminthosporium teres*), bean powdery mildew (*Erysiphe polygoni*), peanut cercospora (*Cercospora arachidicola*), and wheat stem rust (*Puccinia graminis* f. sp. tritici race 15B-2).

5 Claims, No Drawings

SUBSTITUTED ETHYLENE IMIDAZOLE AND TRIAZOLES

This is a continuation of application Ser. No. 06/307,414, filed Oct. 1, 1980, now abandoned.

SUMMARY OF THE INVENTION

This invention relates to compounds of the formula

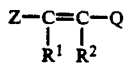
(I)

wherein Z is an aryl group or substituted aryl group; $R^1$ a hydrogen is an alkyl, cycloalkyl, alkenyl, cycloalkenyl, alkynyl, or an aryl or substituted aryl group; $R^2$ is hydrogen, or an aryl or substituted aryl group; Q is 1-imidazolyl, 1- or 4-(1,2,4 triazolyl); and the agronomically acceptable enantiomorphs, geometric isomers, acid addition salts and metal complexes thereof.

DETAILED DESCRIPTION OF THE INVENTION

This invention relates to novel substituted ethylenic imidazoles as well as triazoles and the entantiomorphs, geometric isomers, acid addition salts, and metal salt complexes thereof, as well as their method of preparation and use as broad spectrum systemic fungicides. In particular, this invention relates to compounds of the formula

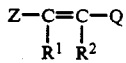
(II)

wherein Z is an optionally substituted phenyl or naphthyl group; $R^1$ is hydrogen, a ($C_1$ to $C_{12}$) alkyl group, a ($C_3$ to $C_8$) cycloalkyl group, a ($C_2$ to $C_8$) alkenyl group, a ($C_5$ to $C_8$) cycloalkenyl group, a ($C_2$ to $C_8$) alkynyl group, or a phenyl or naphthyl or substituted phenyl or naphthyl group; $R^2$ is hydrogen or a phenyl or substituted phenyl group; Q is 1-imidazolyl, 1- or 4-(1,2,4-triazolyl); and the agronomically acceptable enantiomorphs, geometric isomers, acid addition salts and metal salt complexes thereof.

When Z is substituted phenyl or naphthyl, or when $R^1$ is substituted phenyl or naphthyl, or when $R^2$ is substituted phenyl, the aromatic ring may be substituted with up to three substitutents, preferably with up to two substitutents selected from the group consisting of halogen, nitro, trihalomethyl, cyano, ($C_1$ to $C_6$) alkyl, ($C_1$ to $C_6$) alkoxy, ($C_1$ to $C_6$) alkylthio, ($C_1$ to $C_6$) alkylsulfinyl, and ($C_1$ to $C_6$) alkylsulfonyl.

Typically the Z, $R^1$ and $R^2$ moieties encompassed by this invention are phenyl, 2-chlorophenyl, 4-chlorophenyl, 2,4-dichlorophenyl, 2,4-dibromophenyl, 3,5-difluorophenyl, 3,4-dichlorophenyl, 2-chloro-4-iodophenyl, 3-chloro-4-nitrophenyl, 2,4-dinitrophenyl, 3,4,5-trimethylphenyl, 2-nitro-4-methoxyphenyl, 4-ethylphenyl, 2,4-dimethoxyphenyl, 4-trifluoromethylphenyl, 2-nitro-4-trifluoromethylphenyl, 3,5-dimethylthiophenyl, 2-cyano-5-methylphenyl, 2,4-dimethylsulfinylphenyl, 2,4-dimethylsulfonylphenyl, 2-iodo-4-methylphenyl and the like. In addition, typical Z and $R^1$ moieties include naphthyl, 2-chloronaphthyl, 2-nitronaphthyl, 2,4-diiodonaphthyl and the like.

The term "alkyl", as used in defining $R^1$ in this specification and in the claims, includes both straight and branched chain alkyl groups of from one to twelve carbon atoms. Typical alkyl groups which are encompassed by the use of this term in defining this invention are methyl, ethyl, propyl, iso-propyl, n-butyl, sec-butyl, iso-butyl, tert-butyl, pentyl, neopentyl, iso-pentyl, hexyl, heptyl, iso-octyl, nonyl, decyl, iso-decyl, undecyl, dodecyl and the like. As used in defining the permissible substituents for Z, $R^1$ and $R^2$, the term "alkyl" includes methyl, ethyl, n-propyl, iso-propyl, n-butyl, iso-butyl, sec-butyl and tert-butyl.

The acids which can be used in making the acid addition salts of the present invention include hydrochloric, hydrobromic, nitric, sulfinic, phosphoric, hydroiodic, hydrofluoric, perchloric, p-toluenesulfonic, methanesulfonic, acetic, citric, tartaric, malic, maleic, oxalic, fumaric, phthalic and the like.

Another embodiment of this invention is found in the metal salt complexes of the formula

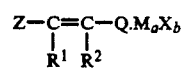
(III)

wherein Z, $R^1$, $R^2$ and Q are as defined in Formula II above, a and b are integers, M is a cation selected from Group IIA, IB, IIB, VIB, or VII of the periodic table, and X is an anionic counterion selected in such a manner that the sum of the valence changes of the a·M cations and the b·X anions equals zero.

Typical cations encompassed by this invention are magnesium, manganese, copper, nickel, zinc, iron, cobalt, calcium, mercury, chromium, lead, barium and the like.

Typical anions encompassed by this invention are chloride, bromide, iodide, fluoride, sulfate, bisulfate, perchlorate, nitrate, nitrite, phosphate, carbonate, bicarbonate, acetate, citrate, oxalate, tartarate, malate, maleate, fumarate, p-toluenesulfonate, methanesulfonate, (mono) or (di) ($C_1$ to $C_4$) alkyldithiocarbamate, ($C_1$ to $C_4$) alkylenebisdithiocarbamate, and the like.

A preferred embodiment of this invention is encompassed by the compounds, enantiomorphs, geometric isomers, salts and complexes of Formulas II and III wherein Z is a phenyl or naphthyl group, preferably a phenyl group, optionally substituted with up to three substituents, preferably with up to two substituents selected from the group consisting of halogen, nitro, trihalomethyl, cyano, ($C_1$ to $C_4$) alkyl, ($C_1$ to $C_4$) alkoxyl, ($C_1$ to $C_4$) alkyl thio; $R^1$ is selected from the group consisting of ($C_1$ to $C_{12}$) alkyl, ($C_5$ to $C_7$) cycloalkyl, ($C_2$ to $C_4$) alkenyl, ($C_2$ to $C_4$) alkynyl, phenyl or phenyl substituted with up to two halogen atoms; $R^2$ is hydrogen or phenyl or phenyl substituted with up to 2 halogen atoms; and Q is imidazolyl, 1- or 4-(1,2,4-triazolyl).

A more preferred embodiment of this invention is encompassed by the compounds, enantiomorphs, geometric isomers, salts and metal salt complexes of Formulas II and III wherein Z is phenyl optionally substituted with up to three substituents, preferably with up to two substitutents, selected from the group consisting of chlorine, bromine, methyl, methoxy, nitro and methylthio; $R^1$ is ($C_1$ to $C_{12}$) alkyl, cyclohexenyl, propargyl, phenyl or mono- or dichloro substituted phenyl; $R^2$ is hydrogen or 4-chlorophenyl; and Q is imidazolyl, or 1-4-(1,2,4)triazolyl.

Typical compounds encompassed by the present invention include:

1-[1,2-di-(2-chlorophenyl)ethenyl] imidazole
1-[2-(2,4-dichlorophenyl)hex-1-enyl] imidazole
1-[2,2-bis(4-chlorophenyl)ethenyl]-1,2,4-triazole
1-[2,2-bis(phenyl)ethenyl] imidazole hydrochloride
1-[2,2-bis(4-chlorophenyl)ethenyl] imidazole hydrochloride
1-[2,2-bis(4-chlorophenyl)ethenyl] imidazole
1-[2,2-bis(phenyl)ethenyl] imidazole
1-[2,2-bis(4-chlorophenyl)ethenyl] imidazole
1-[2-(4-chlorophenyl)-2-(2-chlorophenyl)ethenyl]-1,2,4-traizole
1-[2-(4-chlorophenyl)-2-(4-ethylphenyl)ethenyl]-1,2,4-triazole hydrochloride
1-[2-(4-chlorophenyl)-2-(4-ethylphenyl)ethenyl]-1,2,4-triazole
1-[2,2-bis(4-chlorophenyl)ethenyl]-1,2,4-triazole hydrochloride
1-[2-(4-chlorophenyl)-2-(2-chlorophenylethenyl]-1,2,4-triazole
1-[2-(2,4-dichlorophenyl)-hex-1-enyl]-1,2,4-triazole
1-[2,2-bis(4-ethylphenyl)ethenyl]-1,2,4-triazole
1-[2,2-bis(4-ethylphenyl)ethenyl]-1,2,4-traizole hydrochloride The phenylethenyl imidazoles and triazoles of the present invention can be prepared by standard elimination reactions from the corresponding saturated compounds. A preferred method for preparing the imidazoles and triazoles of the invention is as follows:

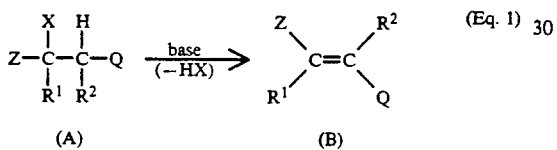

(Eq. 1)

where Z, $R^1$, $R^2$ and Q are defined as in Formula II above and X is halogen, ($C_1$ to $C_8$) alkyl sulfonyl, optionally substituted phenyl sulfonyl optionally substituted on the phenyl ring with up to three substituents selected from the group consisting of halogen and ($C_1$-$C_8$) alkyl or other appropriate leaving group. The base employed can be an organic base such as pyridine, ($C_1$-$C_{12}$) alkyl amine, di-($C_1$-$C_{10}$) alkylamine, tri-($C_1$-$C_{10}$) alkylamine or an inorganic base such as an alkali or alkaline earth metal hydroxides, alkali metal carbonates, or a ($C_1$-$C_{12}$) alkoxide of an alkali metal and the like. The elimination can be performed near or in an inorganic solvent such as dimethylsulfoxide, dimethyl formamide, benzene, toluene, xylene and the like.

The intermediate halide (A) in Equation 1 above can be prepared from the corresponding hydroxide by treatment of the hydroxide with thionyl chloride, methane sulfinyl chloride, phosphorus tribromide and the like:

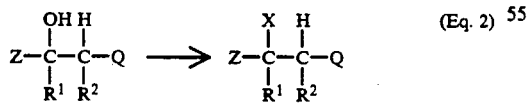

(Eq. 2)

where Z, $R^1$ $R^2$, Q and X are defined above.

The preparation of certain hydroxyphenethyl imidazoles and triazoles useful as starting materials in Equation 2 is described in U.S. patent application Ser. Nos. 820,274, filed Jul. 29, 1977, by H. Chan and G. A Miller and 81,277, filed Oct. 2, 1979, by H. Chan and G. A. Miller and assigned to a common assignee.

For the preparation of the diphenyl ethenyl imidazoles and triazoles of the instant invention, two potential leaving groups are required, one for the generation of the carbon-carbon double bond and the other for the attachment of the azo ring via a substitution reaction. For example, reaction of 2,2-bis(p-chlorophenyl)-1,1-dichloroethane, trademarked RHOTHANE by Rohm and Haas Company, with 50% aqueous sodium hydroxide solution in dimethyl sulfoxide (DMSO) provides vinyl chloride in quantitative yield. Without further purification, vinyl chloride can be used to react directly with imidazole or sodium imidazole to furnish the final product, 2,2-bis(p-chlorophenyl)ethenyl imidazole (Equation 3).

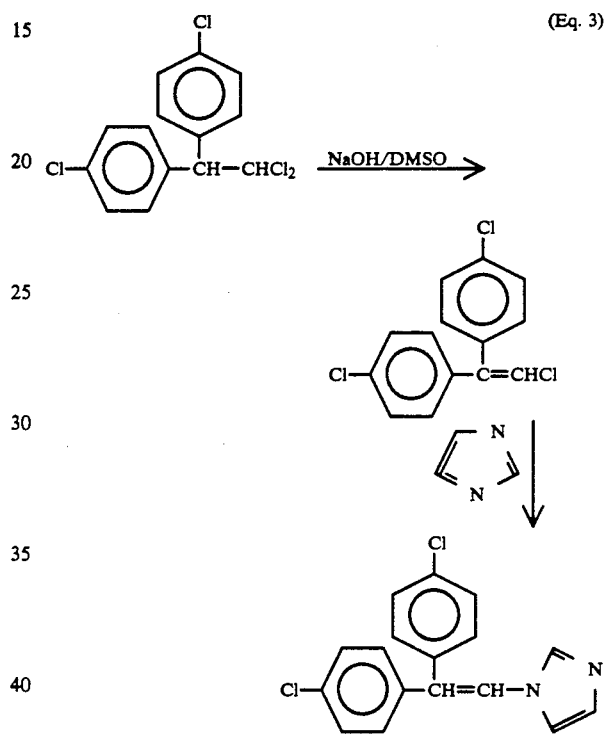

(Eq. 3)

Starting material in this reaction is produced by reacting chlorobenzene with dichloracetaldehyde under the Friedel-Crafts conditions (Equation 4).

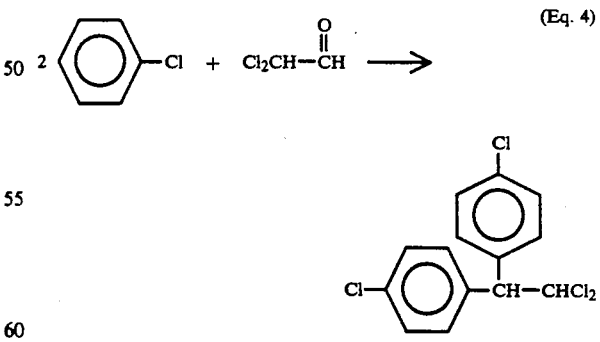

(Eq. 4)

The acid addition salts of the ethylenic imidazoles and triazoles of this invention can be prepared by standard techniques well-known in the art. For example, the compound of Formula (II) can be dissolved in an appropriate solvent such as diethyl ether, tetrahydrofuran, ethanol, methanol, and the like or combinations thereof, and treated with an equivalent or excess amount of a mineral or organic acid which may or may not be dissolved in an appropriate solvent. The mixture is then either cooled or evaporated to give the salt, which can either be used as such or recrystallized from an appropriate solvent or combination of appropriate solvents.

The metal salt complexes of the above ethylenic imidazoles and triazoles can be prepared by adding dropwise, with stirring, a stoichiometric amount of a metal salt dissolved in an appropriate solvent or combination of solvents to a solution of the ethylenic imidazole or triazole of Formula (II) dissolved in a similarly appropriate solvent or combination of solvents. The reaction mixture is briefly stirred and the solvent is removed under reduced pressure to give the metal salt complex of the respective ethylenic imidazole or triazole of Formula (III).

The metal salt complexes can also be prepared by mixing stoichiometric or excess amounts of the metal salt and an ethylenic imidazole or triazole of Formula (II) in the desired amount of solvent containing the appropriate adjuvants just prior to spraying the plants. Adjuvants that may be included in this "in-situ" preparation may be detergents, emulsifiers, wetting agents, spreading agents, dispersing agents, stickers, adhesives, and the like which are used in agricultural applications.

Solvents that can be utilized in these procedures include any polar solvent, e.g., water, methanol, ethanol, isopropanol or ethylene glycol and any aprotic dipolar solvent, e.g., dimethylsulfoxide, acetonitrile, dimethylformamide, nitromethane or acetone.

The metal salt cations that can be used in these procedures can be selected from the group consisting of calcium, magnesium, manganese, copper, nickel, zinc, iron, cobalt, tin, cadmium, mercury, chromium, lead, barium and the like.

Any appropriate anion, e.g., chloride, bromide, iodide, sulfate, bisulfate, phosphate, nitrate, perchlorate, carbonate, bicarbonate, hydrosulfide, hydroxide, acetate, oxalate, malate, citrate and the like may be utilized as the counterion in the metal salt.

Any metal containing fungicides can be used in place of the metal salt. Typical metal containing fungicides that can be utilized in these procedures are: a) dithiocarbamates and derivatives such as: ferric dimethyldithiocarbamate (ferbam), zinc dimethyldithiocarbamate (ziram), manganese ethylenebisdithiocarbamate (maneb) and its coordination product with zinc ion (mancozeb), zinc ethylenebisdithiocarbamate (zineb); b) copper-based fungicides such as cuprous oxide, copper oxychloride, copper naphthenate, and Bordeaux mixture; and c) miscellaneous fungicides such as: phenylmercuric acetate, N-ethylmercuri-1,2,3,6-tetrahydro-3,6-endomethano-3,4,5,6,7,7-hexachlorophthalimide, phenylmercuri monoethanolammonium lactate, nickel-containing compounds and calcium cyanamide.

Some of the compounds of this invention possess an asymmetric carbon atom (i.e., in $R^1$ or $R^2$ of Formula I) and thus exist as racemic mixtures. The d and l enantiomorphs in these racemic mixtures can be separated via standard techniques such as fractional crystallization with d-tartaric acid, l-tartaric acid, l-quinic acid and the like followed by basification and extraction of the d or l enantiomorph free base.

The following examples are provided merely to illustrate the methods of preparation of the compounds of the present invention. These examples are not meant to be considered, in any way, as limitations of the breadth and scope of the present invention. The temperatures expressed in these examples are in degrees centigrade.

EXAMPLE 1

1-[1,2-Di-(2-chlorophenyl)ethenyl] imidzole

A. Preparation of 1-[2-chloro-1,2-di-(2-chlorophenyl)ethyl] imidazole

A solution of 6 g (0.05 mole) of thionyl chloride dissolved in 20 ml of benzene is added dropwise to a solution containing 11 g (0.033 mole) of 1-[2-hydroxy-1,2-di-(2-chlorophenyl)ethyl] imidazole and 150 ml of benzene at room temperature. The reaction mixture is heated to reflux for 3 hours and is then made basic with 10% ammonium hydroxide solution. The organic product is extracted with ether and the combined ether extracts are washed with water, saturated sodium chloride solution, and dried over magnesium sulfate. Solvent is evaporated to give 11 g of a brown oil. This material is further purified by converting to its hydrochloride salt and back neutralized to the free base to give 8.2 g of the expected product.

nmr (CDCl$_3$): δ 6.2–6.6 (two doublets centered around δ 6.4, 2H), 6.7–8.0 (complex multiplets, 11H),

B. Preparation of 1-[1,2-Di-(2-chlorophenyl)ethenyl] imidzole

To a solution containing 3 g of 1-[2-chloro-1,2-di-(2-chlorophenyl)ethyl] imidazole in 20 ml of dimethyl sulfoxide is added 10 ml of 50% sodium hydroxide solution dropwise. The resulting reaction mixture is heated at 60° for 2 hours and poured into 300 ml of water and extracted with ether. The combined ether extracts are washed with water, saturated sodium chloride solution and dried over magnesium. Solvent is evaporated to give 2.5 g of a yellow oil.

EXAMPLE 2

1-[2-(2,4-Dichlorophenyl)hex-1-enyl) imidazole

A. Preparation of 1-[2-Chloro-2-(2,4-dichlorophenyl)hexyl] imidazole

To a solution of 15 g (0.05 mole) of 1-[2-hydroxy-(2,4-dichlorophenyl)hexyl] imidazole (in 100 ml of chloroform is added 6 g (0.05 mole) of thionyl chloride dropwise. After the addition, the reaction is heated to reflux for 8 hours. The reaction mixture is then poured into water and extracted with chloroform. The combined chloroform extracts are washed with 10% ammonium hydroxide solution, water, saturated sodium chloride solution and dried over magnesium sulfate. Solvent is evaporated to give the crude product which can be further purified by converting to its nitric acid salt and back neutralized to its free base to give 12 g of an oily product.

B. Preparation of 1-[2-(2,4-Dichlorophenyl)hex-1-enyl] imidazole

To a solution of 10 g of 1-[2-chloro-2-(2,4-dichlorophenyl)hexyl] imidazole in 100 ml of dimethyl sulfoxide is added 25 ml of 50% sodium hydroxide solution dropwise at room temperature. The reaction mixture is heated at 60° for 2 hours. It is then poured into 300 ml of ice water and extracted with ether. The combined ether extracts are washed with saturated sodium chloride solution and dried over magnesium sulfate. Drying agent is filered and to the filtrate is added concentrated nitric acid dropwise until it is strongly acidic. An oily material settled and is triturated with a 50—50 ether-hexane mixture three times and then back neutralized to its free base with 10% ammonium hydroxide solution. The free base is extracted with ether and the combined ether extracts are washed with water and saturated sodium chloride solution and dried over magnesium sulfate. Solvent is evaporated to give 6 g of a brown oily product.

nmr (CDCl$_3$): δ 0.6–1.5 (m, 7H), 2.6 (t, 2H), 6.6 (s, 1H), 7.0–7.8 (m, 6H).

EXAMPLE 11

1-[2,2-Bis-(p-chlorophenyl)ethenyl]-1,2,4-triazole

A. Preparation of 2,2-Bis(p-chlorophenyl)-1-chloroethylene

Into a 4-necked 2-liter flask are placed 500 g (1.56 mole) of 2,2-bis(p-chlorophenyl)-1,1-dichloroethane and 500 ml of dimethyl sulfoxide. A solution of 188 ml (2.34 mole) of 50% sodium hydroxide is added dropwise. The reaction mixture exotherms to 63° during the addition. After the addition, the reaction mixture is stirred for one hour and poured into ice-water. It is extracted with ether. The combined ether extracts are washed with water, saturated sodium chloride solution, and dried over sodium sulfate. Solvent is evaporated to give 311 g of a waxy solid. A portion of the crude product is recrystalized from hexane-ether to give a white solid, mp 65°–7°.

B. 1-[2,2-Bis(p-clorophenyl)ethenyl]-1,2,4-triazole

Into a 500 ml round bottom flask are charged 12 g (0.17 mole) of 1H-1,2,4-traizole, 11 g (0.17 mole) of 86% powdered potassium hydroxide and 200 ml of diemthyl sulfoxide. The mixture is heated to 140° C. and 100 ml of dimethyl sulfoxide are distilled under reduced pressure followed by dropwise addition of 40 g (0.14) of 2,2-bis (p-chlorophenyl)-1-chloroethylene dissolved in 50 ml of dimethyl sulfoxide. The reaction mixture is heated at 140° C. for one hour, poured into water, and extracted with ether. The combined ether extracts are washed with water, saturated sodium chloride solution, and dried further purified by trituration with n-hexane to give 25 g of the expected product, mp 126°–8°.

nmr (DMSO): δ 7.0–7.6 (M, 8HO, 7.7 (S, 1H), 8.0 (S, 1H), 8.2 (S, 1H),

In TABLE I, the structures of the above-identified representative compounds of this invention and of additional representative compounds of this invention prepared by the methods described above are set forth. In TABLE II, the melting points and elemental analyses of Examples 1–16 are provided.

TABLE I

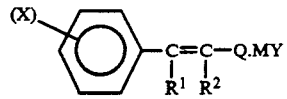

| Example | X | R$^1$ | R$^2$ | Q | MY |
|---|---|---|---|---|---|
| 1 | 2-Cl | H | 2-Cl C$_6$H$_4$ | Imidazole | — |
| 2 | 2,4-Cl$_2$ | n-C$_4$H$_9$ | H | " | — |
| 3 | 4-Cl | 4-Cl C$_6$H$_4$ | " | " | HCl |
| 4 | H | C$_6$H$_5$ | " | " | HCl |
| 5 | H | " | " | " | — |
| 6 | 4-Cl | 4-Cl C$_6$H$_4$ | " | " | — |
| 7 | " | " | " | " | HNO$_3$ |
| 8 | " | 2-Cl C$_6$H$_4$ | " | " | — |
| 9 | 4-C$_2$H$_5$ | 4-(C$_2$H$_5$) C$_6$H$_4$ | " | " | HCl |
| 10 | " | " | " | " | — |
| 11 | 4-Cl | 4-Cl C$_6$H$_4$ | " | 1-Triazole | — |
| 12 | " | " | " | " | — |
| 13 | " | 2-Cl C$_6$H$_4$ | " | " | — |
| 14 | 2,4-Cl$_2$ | n-C$_4$H$_9$ | " | " | — |
| 15 | 4-C$_2$H$_5$ | 4-(C$_2$H$_5$) C$_6$H$_4$ | " | " | HCl |
| 16 | " | " | " | " | — |

TABLE II

| Example | Formula | MP(°C.) | C | H | Cl | N |
|---|---|---|---|---|---|---|
| 1 | C$_{17}$H$_{12}$Cl$_2$N$_2$ | Oil | 64.78(64.79) | 3.84(3.80) | 22.50(22.25) | 8.89(8.49) |
| 2 | C$_{15}$H$_{16}$Cl$_2$N$_2$ | Oil | 61.03(60.88) | 5.46(5.50) | 24.02(24.53) | 9.49(9.27) |
| 3 | C$_{17}$H$_{12}$Cl$_2$.HCl | 240 | 58.06(58.05) | 3.73(3.73) | 30.25(30.41) | 7.97(8.36) |
| 4 | C$_{17}$H$_{14}$N$_2$.HCl | 200–205 | 68.06(68.56) | 7.42(7.29) | 13.39(13.49) | 10.49(10.66) |
| 5 | C$_{17}$H$_{14}$N$_2$ | Oil | 83.25(82.86) | 5.83(5.73) | | 11.24(11.42) |
| 6 | C$_{17}$H$_{12}$Cl$_2$N$_2$ | 93–6 | 64.78(62.94) | 3.84(3.97) | 22.50(21.49) | 8.89(8.58) |
| 7 | C$_{17}$H$_{12}$Cl$_2$N$_2$.HNO$_3$ | 147–9 | 53.99(53.58) | 3.46(3.62) | 18.75(18.34) | 11.11(11.58) |
| 8 | C$_{17}$H$_{12}$Cl$_2$N$_2$ | 66–70 | 64.78(65.64) | 3.84(3.97) | 22.50(21.89) | 8.89(8.91) |
| 9 | C$_{21}$H$_{22}$N$_2$HCl | 210 | 74.13(74.43) | 6.87(6.84) | 10.61(10.46) | 8.36(8.27) |
| 10 | C$_{21}$H$_{22}$N$_2$ | Oil | 81.61(83.40) | 7.29(7.33) | | 8.90(9.27) |
| 11 | C$_{16}$H$_{11}$Cl$_2$N$_3$ | 126–8 | 60.78(60.72) | 3.51(3.45) | 22.42(22.20) | 13.29(13.24) |
| 12 | C$_{16}$H$_{11}$Cl$_2$N$_3$.HCl | 185–190 | 54.49(54.17) | 3.43(3.37) | 30.16(30.44) | 11.92(11.68) |
| 13 | C$_{16}$H$_{11}$Cl$_2$N$_3$ | Oil | 60.78(60.27) | 3.51(3.52) | 22.42(22.37) | 13.29(12.45) |
| 14 | C$_{14}$H$_{15}$Cl$_2$N$_3$ | Oil | 56.77(54.65) | 5.10(5.70) | 23.94(21.98) | 14.19(10.86) |
| 15 | C$_{20}$H$_{21}$N$_3$.HCl | 166–169 | 70.15(70.68) | 6.66(6.52) | 10.39(10.44) | 12.02(12.37) |
| 16 | C$_{20}$H$_{21}$N$_3$ | Oil | 78.46(79.17) | 7.06(6.98) | | 13.50(13.85) |

The ethylenic imidazoles and triazoles, enantiomorphs, acid addition salts and metal salt complexes of this invention are broad-spectrum fungicides which possess a high degree of activity against assorted phytopathogenic fungi. These compounds, enantiomorphs, salts and complexes are particularly effective at rates of application from about 50 to about 2000 ppm in controlling barley net blotch (*Helminthosporium teres*) on barley plants, chocolate spot (*Botrytis fabae*) on faba beans, bean powdery mildew (*Erysiphe polygoni*) on bean plants, grape downy mildew (*Plasmopora viticola*) on grape seedlings, peanut cercospora (*Cercospora arachidicola*) on peanuts, rice blast, (*Piricularia oryzae*) on rice plants, tomato late blight (*Phytophthora infestans*) on tomato seedlings, and wheat stem rust (*Puccinia graminis* f. sp. *tritici* race 15B-2) on wheat seedlings.

In evaluating these compounds, a preliminary fungicidal evaluation is carried out using the compounds at 300 ppm and spraying the plants to run off in a carrier volume of about 150 gallons/acre.

The general procedure is to take potted plants in proper condition of growth for susceptibility to the fungal disease to be evaluated, apply chemical solution to run off, and allow them to dry. The plants are then inoculated with fungal spores and then allowed to incubate until the disease has developed and the percent control can be read or estimated.

The following test methods are employed in evaluating the fungicidal activity of the compounds, enantiomorphs, salts and complexes of this invention.

EXAMPLE A

Barley Net Blotch (*Helminthosporium teres*)

Barley plants (var. Besbar or Wong) are trimmed to a height approximately 2½ inches, 24 hours prior to chemical application. This procedure provides plants of a uniform height and permits rapid inoculation of treated plants.

*Helminthosporium teres* is cultured on potato-dextrose agar (PDA) slants for 14 days at ambient temperature and low light intensity. spores are harvested by adding deionised water to the PDA slants and scraping the agar surface with a rubber policeman or similar blunt object. The spore suspension is filtered through cheesecloth to remove mycelial and agar fragments and then adjusted to a concentration of 15-20,000 spores/ml. One drop (0.5 ml) of Tween 80 is added to 100 cc inoculum to provide a more even spore distribution on the surface of the barley leaves.

The barley plants are inoculated by spraying the foliage of the plants with a hand sprayer until small droplets of the inoculum are observed on the leaves. Inoculated plants are incubated in a humid environment at 75°-80° F. for 24 hours prior to being placed in the greenhouse at 70°-75° F.

Treatment comparisons are made 6–7 days after inoculation. Typical barley net blotch symptoms initially appear as irregular sunken watersoaked areas which become necrotic as the lesions enlarge.

Certain of the ethylenic imidazoles and triazoles of this invention demonstrate complete control over *Helminthosporium teres* at an application rate of 300 ppm.

EXAMPLE B

Chocolate Spot of Broad Beans (*Botrytis fabae*) (BOT)

Broad bean (*Vicia faba*) are trimmed to a height of approximately 4½ inches, 24 hours prior to chemical application. This procedure provides plants of a uniform height and permits rapid and uniform inoculation of treated plants.

*Botrytis fabae* is cultured on oatmeal agar (OA) slants for 21 days at ambient temperature and low intensity. Spores are harvested by adding deionized water to the OA slants and scraping the agar surface with a rubber policeman or similar blunt object. The spore suspension is filtered through cheesecloth to remove mycelial and agar fragments and then adjusted to a concentration of 175-200,000 spores per ml with an inoculation medium. The inoculation medium (20 gms glucose, 1 gm ammonium phosphate, 2 gm potassium nitrate, 10 mgm ascorbic acid, 1500 ml deionized water and 500 ml apple juice) is to provide improved spore germination on the surface of the broad bean leaves and stems.

Broad bean plants are inoculated by spraying the foliage with the fungicide group's overhead mechanical sprayer. Inoculated plants are incubated in a humid environment at 75°-85° F. for 66 hours.

Treatment comparisons are made 66–68 hours after inoculation. Typical broad bean chocolate leaf spot symptoms appear as regular circular to lanceolate lesions on plant leaves and stems.

Certain of the ethylenic imidazoles and triazoles of this invention demonstrate greater than 90% control over *Botrytis fabae* at an application rate of 300 ppm.

EXAMPLE C

Bean Powdery Mildew (*Erysiphe polygoni*) (BPM)

Bean plants (var. Dwarf Hort) are thinned to two plants per pot 24 hours prior to chemical application.

*Erysiphe polygoni* is cultured on bean leaves for 10-21 days under existing greenhouse conditions. Spores are harvested by adding deionized water containing 0.5 ml of Tween 80 per 500 ml water to a quart jar containing excised mildew infested bean leaves. The spores are loosened from the leaf surface by shaking the jar. The resulting suspension is filtered through cheesecloth to remove plant debris and adjusted to $2-2.5 \times 10^4$ spores per ml.

Bean plants are inoculated by spraying the leaves and stems with inoculum until a uniform film of inoculum is observed on the plant. Inoculated plants are maintained under existing greenhouse conditions.

Treatment comparisons are made 8–10 days after inoculation. Typical bean powder mildew signs are circular white mycelial mats (fructifications) on the leaf surface.

The majority of the ethylenic imidazoles and triazoles of this invention demonstrate complete control over *Erysiphe polygoni* at an application rate of 300 ppm.

EXAMPLE D

Grape Downy Mildew (*Plasmopora viticola*) (GDM)

Grape seedlings 4–5 inches tall are used.

*Plasmopora viticola* is cultured on grape leaves for 7 days at 65°-75° F. in a growth room at moderate light intensity. Spores are harvested by adding deionized water and scraping the leaf surface with a camels hair brush. The spore suspension is filtered through cheesecloth to remove plant debris and adjusted to a concentration of 100-125,000 spores per ml.

The grape plants are inoculated by spraying the leaves with a hand held air brush until small uniform droplets of inoculum are observed on the leaves. The inoculated plants are incubated in a humid environment at 65°-70° F. for 48 hours prior to being placed in a growth room.

Treatment comparisons are made 7 days after inoculation. Typical grape downy mildew symptoms appear on the upper leaf surface as pale-yellow spots variable in size and form, frequently circular without a distinct line of demarcation. Under humid conditions the lower leaf surface is covered by conspicuous fungal growth.

Certain of the ethylenic imidazoles and triazoles of this invention possess greater than 90% control over *Plasmopora viticola* at an application rate of 300 ppm.

EXAMPLE E

Cercospora Leafspot of Peanut (*Cercospora arachidicola*) (PC)

Peanut plants (var. Tamnut 74) are 14 days-old when treated.

*Cercospora arachidicola* is cultured on peanut-oatmeal agar (POA) in petri plates for 14 days under fluorescent lights that are 20 cm above the cultures. These petri plates are inoculated with 0.5 ml of a spore suspension made in sterile water containing a few drops of Tween 80. The spore suspension is subsequently spread over the surface of the POA plate by means of a sterile glass rod bent in the form of a hockey stick. Spores are harvested from plates by adding deionized water containing a small amount of Tween 80 to the POA plates. The agar surface is spaced with a rubber policeman or similar blunt object. The spore suspension is filtered through cheesecloth to remove mycelial and agar fragments and then adjusted to a concentration of 75,000–100,000 spores per ml.

Treated peanut plants are inoculated by spraying the leaves with inoculum until a uniform film of inoculum is observed on the plant. Inoculated plants are incubated in a humid environment at 85°-90° F. for 72 hours. They are removed from the humid environment, allowed to dry, and placed under existing greenhouse conditions.

Treatment comparisons are made 10-14 days after inoculation. Typical Cercospora leafspot symptoms are brown to dark circular spots usually surrounded by a yellow halo.

Certain of the ethylenic imidazoles and triazoles of this invention demonstrate complete control of *Cercospora arachidicola* at application rate of 300 ppm.

EXAMPLE F

Rice Blast (*Piricularia oryzae*) (RB)

Rice plants (var. Nova 66) are trimmed to a height of approximately 5 inches, 24 hours prior to chemical application. This procedure provides plants of uniform height and permits rapid inoculation of treated plants.

*Piricularia oryzae* is cultured on wheat dextrose agar (WDA) plates for 14 days at ambient temperature and normal room light intensity. Spores are harvested by adding deionized water containing 2 g gelatin and surface with a rubber policeman or other similar blunt object. The spore suspension is filtered through cheesecloth to remove mycelial and agar fragments and then adjusted to a concentration of $7.5-10 \times 10^4$ spores/ml.

Rice plants are inoculated by spraying the leaves and stems with an air brush until a uniform film of inoculum is observed on the leaves. The inoculated plants are incubated in a humid environment (75°-85° F.) for 24 hours prior to being placed in a greenhouse environment.

Treatment comparisons are made 7-8 days after inoculation. Initial rice blase lesions appear as small brown necrotic spots on the foliage. The typical lesion is eliptical, 1-2 cm with a large necrotic gray center and brown margins.

Certain of the ethylenic imidazoles and triazoles of this invention demonstrate greater than 90% control of *Piricularia oryzae* at an application rate of 300 ppm.

EXAMPLE G

Tomato Late Blight (*Phytophthora infestans*) (TLB)

Tomato (var. Rutgers) seedlings, 2½-3 inches tall, are fertilized with a water soluble fertilizer 4-5 days prior to chemical application to promote rapid succulent growth and better symptom expression.

The pathogen is grown on lima bean agar for 12-15 days at 60° F. and the fungal growth is removed by the agitation of a rubber policeman on a glass rod over the surface of the agar in the presence of deionized water. The inoculum is strained through cheesecloth to remove mycelial and agar fragments and the spore concentration adjusted to 50-60,000 spores/ml.

The spore suspension is applied with a DeVilbiss atomizer at 8-10 psi air pressure on the leaf undersurface until fire driplets are formed.

Inoculated seedlings are placed in a humid environment at 60°-62° F. for 40-45 hours, prior to being placed in the greenhouse at 70°-75° F.

Treatment comparisons are made 5-6 days after inoculation. Initially, typical tomato late blight symptoms appear as irregular, greenish-black, water-soaked patches which enlarge and become brown, with a firm corrugated surface. Severe infection will resemble frost damage.

Certain of the ethylenic imidazoles and triazoles of this invention demonstrate greater than 70% control of *Phytophthora infestans* at an application rate of 300 ppm.

EXAMPLE H

Wheat Stem Rust (*Puccinia graminis* f. sp. *tritici* race 15B-2) (WSR)

Seven-day-old wheat plants (var. Wanser) are trimmed to approximate 2¼ inches, 24 hours prior to chemical application to provide a uniform plant height and to facilitate uniform inoculation.

Wheat stem rust is cultured on wheat (var. Wanser) seedlings for a period of 14 days under existing greenhouse conditions.

A spore suspension of *Puccinia graminis* f. sp. *tritici* race 15B-2 is made by excising infected wheat leaves and placing the leaves into a pint jar containing water and the surfactant "Tween 80" (1 drop/100 cc). The surfactant serves to free the rust urediospores from the sori and improves inoculum retention when applied to plant foliage. The resulting spore suspension is filtered through cheesecloth to remove the leaves and assorted other plant debris. The spore concentration is not adjusted, but a minimum of $2.5 \times 10^4$ spores per mil are required to obtain an acceptable disease level.

Wheat plants are inoculated by applying the stem rust spore suspension until run-off, with a DeVilbiss atomizer at 5 psi air pressure. After inoculation, the plants are placed into a humid environment at approximately 68° F. A timer is used to permit 12 hours of continuous darkness followed by a minimum of 3-4 hours of light with an intensity of 500 ft. candles. The temperature in the chamber should not exceed 85° F. At the end of the light period, the fogger is turned off and vented to allow the plants to dry slowly prior to being placed into a greenhouse environment.

The plants are permitted to grow under greenhouse condition for a period of 2 weeks prior to making treatment comparisons. Wheat stem rust is characterized by brick red spores in irregularly shaped sori on the leaves and stems of the wheat seedlings.

Certain of the ethylenic imidazoles and triazoles of this invention exhibit complete control of *Puccinia graminis* at an application rate of 300 ppm.

The results of testing Examples 1 through 16 are summarized in Table III.

TABLE III

| | Fungicide Test Results | | | | | | | |
|---|---|---|---|---|---|---|---|---|
| Example | BH | BOT | BPM | GDM | PC | RB | TLB | WSR |
| 1 | E | C | A | E | — | — | — | E |
| 2 | A | E | A | E | — | E | E | E |
| 3 | B | C | C | E | — | C | C | E |
| 4 | E | E | E | E | E | E | E | A |
| 5 | A | E | B | C | E | C | E | A |
| 6 | B | E | E | C | — | E | C | A |

TABLE III-continued

| | Fungicide Test Results | | | | | | | |
|---|---|---|---|---|---|---|---|---|
| Example | BH | BOT | BPM | GDM | PC | RB | TLB | WSR |
| 7  | A | E | B | E | — | E | E | A |
| 8  | A | C | A | B | B | B | C | B |
| 9  | E | B | E | E | E | E | E | E |
| 10 | C | B | C | E | E | E | E | C |
| 11 | A | E | A | E | — | E | E | A |
| 12 | A | E | A | E | — | E | E | A |
| 13 | A | E | A | B | A | A | C | A |
| 14 | A | E | A | E | A | E | E | A |
| 15 | E | C | A | E | E | E | E | E |
| 16 | E | E | A | E | E | E | E | E |

In compiling this table, the following codes are used:

BH = Barley Net Blotch (*Helminthosporium teres*)
BOT = Chocolate Sot of Broad Beans (*Botrytis fabae*)
BMP = Bean Powdery Mildew (*Erysiphe polygoni*)
GDM = Grape Downy Mildew (*Plasmopora viticola*)
PC = Peanut Cercospora (*Cercospora arachidicca*)
RB = Rice Blast (*Piricularia oryzae*)
TLB = Tomato Late Blight (*Phytophthora infestans*)
WSR = Wheat Stem Rust (*Puccinia graminis* f. sp. *tritici* race 15B-2)

The following disease rating scale is used for evaluating these fungicidal agents:

| | |
|---|---|
| A = | 97-100% disease control |
| B = | 90-96% disease control |
| C = | 70-80% disease control |
| D = | 50-60% disease control |
| E = | 50% disease control |

The ethylenic imidazoles are triazoles, enantiomorphs, geometric isomers, acid addition salts and metal salt complexes of the present invention are useful as agricultural fungicides and as such can be applied to various loci such as the seed, the soil or the foliage. For such purposes these compounds can be used in the technical or pure form as prepared, as solutions or as formulations. The compounds are usually taken up in a carrier or are formulated so as to render them suitable for subsequent dissemination as fungicides. For example, these chemical agents can be formulated as wettable powders, emulsifiable concentrates, dusts, granular formulations, aerosols, or flowable emulsion concentrates. In such formulations, the compounds are extended with a liquid or slid carrier and, when desired, suitable surfactants are incorporated.

It is usually desirable, particularly in the case of foliar spray formulations, to include adjuvants, such as wetting agents, spreading agents, dispersing agents, stickers, adhesive and the like in accordance with agricultural practices. Such adjuvants commonly used in the art can be found in the John W. McCutcheon, Inc. publication "Detergents and Emulsifiers, Annual."

In general, the compounds of this invention can be dissolved in certain solvents such as acetone, methanol, ethanol, dimethylformamide, pyridine or dimethyl sulfoxide and such solutions can be extended with water. The concentrations of the solution can vary from about 1% to about 90% with a preferred range being from about 5% to about 50%.

For the preparation of emulsifiable concentrates, the compound can be dissolved in suitable organic solvents, or mixtures of solvents, together with an emulsifying agent which permits dispersion of the fungicide in water. The concentration of the active ingredient in emulsifiable concentrates is usually from about 10% to about 90% and in flowable emulsion concentrates, this can be as high as about 75%.

Wettable powders suitable for spraying can be prepared by admixing the compound with a finely divided solid, such as clays, inorganic silicates and carbonates, and silicas and incorporating wetting agents, sticking agents, and/or dispersing agents in such mixtures. The concentration of active ingredients in such formulations is usually in the range of from about 20% to about 98%, preferably from about 40% to about 75%. A typical wettable powder is made by blending 50 parts of 1-[2-(2,4-dichlorophenyl) hex-1-enyl] imidazole, 45 parts of a synthetic precipitated hydrated silicon dioxide sold under the trademark Hi-Sil®, and 5 parts of sodium lignosulfonate. In another preparation a kaolin type (Barden) clay is used in place of the Hi-Sil in the above wettable powder, and in another such preparation 25% of the Hi-Sil is replaced with a synthetic sodium silico aluminate sold under the trademark Zeolox®7.

Dusts are prepared by mixing the ethylenic imidazoles and triazoles, enantiomorphs, salts and complexes thereof with finely divided inert solids which can be organic or inorganic in nature. Materials useful for this purpose include botanical flours, silicas, silicates, carbonates and clays. One convenient method of preparing a dust is to dilute a wettable powder with a finely divided carrier. Dust concentrates containing from about 20% to about 80% of the active ingredient are commonly made and are subsequently diluted to from about 1% to about 10% use concentration.

The ethylenic imidazoles and triazoles, enantiomorphs, geometric isomers, salts and complexes thereof can be applied as fungicidal sprays by methods commonly employed, such as conventional high-gallonage hydraulic sprays, low-gallonage sprays, air-blast spray, aerial sprays and dusts. The dilution and rate of application will depend upon the type of equipment employed, the method of application and diseases to be controlled, but the preferred effective amount is usually from about 0.1 lb. to about 50 lbs. per acre of the active ingredient.

As a seed protectant, the amount of toxicant coated on the seed is usually at a dosage rate of from about 0.1 to about 20 ounces per hundred pounds of seed. As a solid fungicide the chemical can be incorporated in the soil or applied to the surface usually at a rate of from about 0.25 to about 10 lbs. per acre.

Fungicides which can be combined with the fungicides of this invention includes:

(a) dithiocarbamate and derivatives such as: ferric dimethyldithiocarbamate (ferbam), zinc dimethyldithiocarbamate (ziram), manganese ethylenebisdithiocarbamate (maneb) and its coordination product with zinc ion (mancozeb), zinc ethylenebisdithiocarbamate (zineb), zinc propylenebisdithiocarbamate (propineb), sodium methyldithiocarbamate (metham), tetramethylthiuram disulfide (thiram), the complex of zineb and polyethylene thiuram disulfide, 3,5-dimethyl-1,3,5-2H-tetrahydrothiadiazine-2-thione (dazomet); and mixtures of these and mixtures with copper salts;

(b) nitrophenol derivatives such as: dinitro-(1-methylheptyl) phenyl crotonate (dinocap), 2-sec-butyl-4,6-dinitrophenyl 3,3-dimethylacrylate (binapacryl), and 2-sec-butyl-4,6-dinitrophenyl isopropyl carbonate;

(c) heterocyclic structures such as: N-trichloromethylthiotetrahydrophthalimide (captan), N-trichloromethylthiophthalimide (folpet), 2-heptadecyl-2-imidazole acetate (glyodine), 2-octylisothiazol-3-one, 2,4-dichloro-6-(o-chloroanilino)-s-triazine, diethyl phthalimidophosphorothioate, 4-butyl-1,2,4-triazole, 5-amino-1-[bis(dimethylamino)phosphinyl]-3phenyl-1,2,4-triazole, 5-methyl 1-(butylcarbamoyl)-2-benzimidazole carbamate (benomyl), 2-(4'-thiazolyl) benzimidazole (thiabendazole), 4-(2-chlorophenylhydrazono)-3-methyl-5-isoxazolone, pyridine-2-thiol-1-oxide, 8-hydroxyquinoline sulfate and metal salts thereof; 2,3-dihydro-5-carboxanilido-6-methyl-1,4-oxathiin-4,4-dioxide, 2,3-dihydro-5-carboxanilido-6-methyl-1,4-oxathiin,α-(phenyl)-α-(2,4-diclorophenyl)-5-pyrimidinyl-methanol (triarimol), cis-N-[1,1,2,2-tetrachloroethyl)thio]-4-cyclohexane-1,2-dicarboxyimide, 3-[2-(3,5-dimethyl-2-oxycyclohexyl-2-hydroxy]-glutarimide (cycloheximide), dehydroacetic acid, N-(1,1,2,2-tetrachloroethylthio)-3a,4,7,,7a-tetrahydrophthalimide (captafol), 5-butyl-2-ethylamiono-4-hydroxy-6-methylpyrimidine (ethirimol), acetate of 4-cyclododecyl-2,6-dimethylmorpholine (dodemorph), and 6-methyl-2-oxo-1,3-dithiolo[4,5-b]quinoxaline (quinomethionate).

(d) miscellaneous halogenated fungicides such as: tetrachloro-p-benzoquinone (chloranil), 2,3-dichloro-1,4-naphthoquinone (dichlone), 1,4-dichloro-2,5-dimethoxybenzene (chloroneb), 3,5,6-trichloro-o-anisic acid (tricamba), 2,4,5,6-tetrachloroisophthalonitrile (TCPN), 2,6-dichloro-4-nitroaniline (dichloran), 2-chloro-1-nitropropane, polychloronitrobenzenes such as: pentachloronitrobenzene (PCNB) and tetrafluorodichloroacetone;

(e) fungicidal antibiotics such as: griseofulvin, kasugamycin and streptomycin;

(f) copper-based fungicides such as: cuprous oxide, basic cupric chloride, basic copper carbonate, copper naphthenate, and Bordeaux mixture; and (g) miscellaneous fungicides such as: diphenyl, dodecylguanidine acetate (dodine), phenylmercuric acetate, N-ethylmercuri-1,2,3,6-tetrahydro-3,6-endomethano-3,4,5,6,7,7,-hexachlorophthalimide, phenylmercuric monoethanol ammonium lactate, p-dimethylaminobenzenediazo sodium sulfonate, methyl isothiocyanate, 1-thiocyano-2,4-dinitrobenzene, 1-phenylthiosemicarbazide, nickel-containing compounds, calcium cyanamide, lime sulfure,sulfur, and 1,2-bis(3-methoxycarbonyl-2-thioureido) benzene (thiophanatemethyl).

The ethylenic imidazoles and triazoles, enantiomorphs, acid addition salts and metal salt complexes of this invention can be advantageously employed in various ways. Since these compounds possess broad spectrum fungicidal activity, they can be employed in the storage of cereal grain. These complexes can also be employed as fungicides in turf, fruit orchards, vegetables and golf course applications. Other applications of the ethylenic imidazoles and triazoles of this invention will suggest themselves to those skilled in the art of agriculture and horticulture.

We claim:

1. A compound 1-[2-(2,4-dichlorophenyl) hex-1-enyl]-1,2,4-triazole.

2. A fungicidal composition for controlling phytopathogenic fungi which comprises, an agronomically acceptable carrier and an active ingredient, a fungicidally effective amount of 1-[2-(2,4-dichlorophenyl)hex-1-enyl]-1,2,4-triazole.

3. A method for controlling phytopathogenic fungi which consists of applying to a plant, to plant seed or to plant habitat, a fungicidally effective amount of 1-[2-(2,4-dichlorophenyl) hex-1-enyl.

4. A compound of the formula

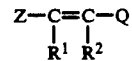

wherein:

Z is phenyl or naphthyl or phenyl or naphthyl substituted with up to three substituents selected from the group consisting of halogen, nitro, trihalomethyl, cyano, $(C_1-C_6)$alkyl, $(C_1-C_6)$alkoxy, $(C_1-C_6)$alkylthio, $(C_1-C_6)$alkylsulfinyl and $(C_1-C_6)$alkylsulfonyl;

$R^1$ is $(C_1-C_{12})$alkyl, $(C_3-C_8)$cycloalkyl, $(C_2-C_8)$alkenyl, $(C_5-C_8)$cycloalkenyl, $(C_2-C_8)$alkynyl, phenyl, naphthyl, or phenyl or naphthyl substituted with up to three substituents selected from the group consisting of halogen, nitro, trihalomethyl, cyano, $(C_1-C_6)$alkyl, $(C_1-C_6)$alkoxy, $(C_1-C_6)$alkylthio, $(C_1-C_6)$alkylsulfinyl, and $(C_1-C_6)$alkylsulfonyl;

$R^2$ is phenyl or phenyl substituted with from one to three substituents selected from the group consisting of halogen, nitro, trihalomethyl, cyano, $(C_1-C_6)$alkyl, $(C_1-C_6)$alkoxy, $(C_1-C_6)$alkylthio, $(C_1-C_6)$alkylsulfinyl, and $(C_1-C_6)$alkylsulfonyl;

Q is 1-imidazolyl, or 1- or 4-(1,2,4-triazolyl); and the agronomically acceptable enantiomorphs, geometric isomers, acid addition salts and metal salt complexes containing at least one metal cation selected from the group consisting of magnesium, manganese, copper, nickel, zinc, iron, cobalt, calcium, mercury, chromium, lead and barium thereof.

5. A compound of the formula

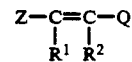

wherein:

Z is phenyl or naphthyl or phenyl or naphthyl substituted with up to three substituents selected from the group consisting of halogen, nitro, trihalomethyl, cyano, $(C_1-C_6)$alkyl, $(C_1-C_6)$alkoxy, $(C_1-C_6)$alkylthio, $(C_1-C_6)$alkylsulfinyl and $(C_1-C_6)$alkylsulfonyl;

$R^1$ is hydrogen;

$R^2$ is phenyl substituted with from one to three substituents selected from the group consisting of halogen, nitro, trihalomethyl, cyano, $(C_1-C_6)$alkyl, $(C_1-C_6)$alkoxy, $(C_1-C_6)$alkylthio, $(C_1-C_6)$alkylsulfinyl, and $(C_1-C_6)$alkylsulfonyl;

Q is 1-imidazolyl, or 1- or 4-(1,2,4-triazolyl); and the agronomically acceptable enantiomorphs, geometric isomers, acid addition salts and metal salt complexes thereof.

* * * * *